(12) United States Patent
Sakaguchi et al.

(10) Patent No.: US 10,123,917 B2
(45) Date of Patent: Nov. 13, 2018

(54) DISPOSABLE DIAPER

(71) Applicant: UNICHARM CORPORATION, Shikokuchuo-shi, Ehime (JP)

(72) Inventors: Satoru Sakaguchi, Kanonji Kagawa (JP); Kana Sawa, Kanonji Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 1098 days.

(21) Appl. No.: 14/385,053

(22) PCT Filed: Mar. 28, 2013

(86) PCT No.: PCT/JP2013/059247
§ 371 (c)(1),
(2) Date: Sep. 12, 2014

(87) PCT Pub. No.: WO2013/147016
PCT Pub. Date: Oct. 3, 2013

(65) Prior Publication Data
US 2015/0100036 A1    Apr. 9, 2015

(30) Foreign Application Priority Data
Mar. 30, 2012   (JP) ................................. 2012-081143

(51) Int. Cl.
*A61F 13/15*        (2006.01)
*A61F 13/534*       (2006.01)
(Continued)

(52) U.S. Cl.
CPC ........ *A61F 13/534* (2013.01); *A61F 13/5633* (2013.01); *A61F 13/62* (2013.01);
(Continued)

(58) Field of Classification Search
CPC ........ A61F 13/53; A61F 13/56; A61F 13/534; A61F 13/5633; A61F 13/62;
(Continued)

(56) References Cited

U.S. PATENT DOCUMENTS

| 6,702,800 B1 | 3/2004 | Vukos et al. |
| 2007/0208319 A1* | 9/2007 | Minato ............... A61F 13/4942 604/385.26 |

(Continued)

FOREIGN PATENT DOCUMENTS

| JP | 9-154883 A | 6/1997 |
| JP | 2004-057413 A | 2/2004 |

(Continued)

OTHER PUBLICATIONS

Office Action in GCC Application No. GC 2013-23988, dated Jun. 8, 2017.

(Continued)

*Primary Examiner* — Jacqueline Stephens
(74) *Attorney, Agent, or Firm* — Hauptman Ham, LLP

(57) ABSTRACT

An absorber 40 of a disposable diaper 10 includes a first region extending from an end at the side of the front waistline region of the absorber towards the side of the crotch region, and a second region arranged adjacent to the first region at the side of the crotch region from the first region, and having a lower bending rigidity than the first region. A boundary between the first region and the second region is arranged at the side of the front waistline region from the end at the side of the front waistline region of the leg stretch units, and is arranged at the side of the crotch region from the end at the side of the crotch region of the target unit.

6 Claims, 5 Drawing Sheets

(51) Int. Cl.
*A61F 13/62* (2006.01)
*A61F 13/56* (2006.01)
*A61F 13/49* (2006.01)

(52) U.S. Cl.
CPC .. *A61F 13/625* (2013.01); *A61F 2013/49088* (2013.01); *A61F 2013/49092* (2013.01); *F04C 2270/0421* (2013.01)

(58) Field of Classification Search
CPC .......... A61F 13/625; A61F 2013/49088; A61F 2013/49092; F04C 2270/0421
USPC .................. 604/378, 380, 385, 101, 385.03
See application file for complete search history.

(56) References Cited

U.S. PATENT DOCUMENTS

2008/0103467 A1* 5/2008 Wallstrom ........ A61F 13/47218
604/380
2013/0296819 A1* 11/2013 Kikuchi ................ A61F 13/496
604/380

FOREIGN PATENT DOCUMENTS

JP 2007-268253 A 10/2007
JP 2008-253289 A 10/2008

OTHER PUBLICATIONS

Extended European Search Report dated Nov. 3, 2015, corresponding to European Patent Application No. 13769858.5.
Office Action dated May 6, 2015, corresponding to Chinese patent application No. 201380015983.X.
Office Action in GCC Application No. 2013-23988, dated Jul. 12, 2016.
Office Action in EG Application No. 1553/2014, dated Aug. 25, 2016.
Office Action in AU Application No. 2013241160, dated Nov. 10, 2016.
Japanese Office Action dated Mar. 5, 2013 in corresponding Japanese Application No. 2012-081143 filed Mar. 30, 2012.
International Search Report dated May 21, 2013 in International Application No. PCT/JP2013/059247 filed Mar. 28, 2013.
Office Action in EG Application No. 2014091553, dated Sep. 6, 2017, 10pp.

* cited by examiner

DISPOSABLE DIAPER

RELATED APPLICATIONS

The present application is a National Phase of International Application Number PCT/JP2013/059247, filed Mar. 28, 2013, which claims priority to Japanese Application Number 2012-081143, filed Mar. 30, 2012.

TECHNICAL FIELD

The present invention relates to a disposable diaper.

BACKGROUND ART

Conventionally, there is known a disposable diaper which has a front waistline region, a rear waistline region, a crotch region, a pair of leg hole openings, an absorber running across a crotch region and extending towards the front waistline region and rear waistline region, and a fastening tape provided in the rear waistline region. A disposable diaper thus configured can be easily worn by securing the fastening tape to the target portion of the front waistline region, and is therefore used widely for newborns, and infants and toddlers.

Furthermore, due to the occurrence of leakage of bodily fluid and the stimulation provided due to an unwanted portion of the diaper coming in contact with the skin of the wearer as a result of shifting of the position of the disposable diaper at the time of wearing, there is known a structure in which it is difficult to unsecure the fastening tape (for example, see Patent Literature 1).

The disposable diaper of Patent Literature 1 is configured such that a convex member is provided as a target tape in the rear waistline region, a concave member in which the convex member is engaged is provided in the front waistline region, a buffering member is provided in the back side of the concave member, thus making it difficult for the convex member and the concave member to be disengaged.

CITATION LIST

Patent Literature

[PTL 1] Japanese Unexamined Patent Application Publication No. H09-154883

SUMMARY OF INVENTION

However, the above disposable diaper had the problems described below.

The convex member and the concave member of the disposable diaper are not easily disengaged, and thus, it is often difficult for the disposable diaper to be deformed with following the movement of the wearer. The convex member and the concave member are not easily disengaged, and as a result, it conversely gives rise to a stimulus to the skin.

Furthermore, upon investigation of the wearing situation of the disposable diaper, the applicants found out that when the diaper was worn, a crease was formed in the front waistline region where the target tape was secured, and the crease unsecured the target tape.

The present disclosure has been achieved in view of this condition, and an object thereof is to provide a disposable diaper, with which it is possible to maintain the secured state of the fastening tape while preventing stimulation to the skin of the wearer.

The disposable diaper (disposable diaper 10) according to the present disclosure is summarized as a disposable diaper, including: a front waistline region (front waistline region 20); a rear waistline region (rear waistline region 30); a crotch region (crotch region 25) positioned between the front waistline region and the rear waistline region; an absorber (an absorber 40) running across the crotch region and extending in the front waistline region and the rear waistline region; a pair of fastening tapes (fastening tapes 90) extending from the rear waistline region to both outer sides in the product widthwise direction; a target unit (target unit 95) arranged at least partially in an absorber-arranged region in which the absorber is arranged, in the front waistline region, and where each of the pair of the fastening tapes is secured, a product longitudinal direction (a product longitudinal direction L) from the front waistline region towards the rear waistline region; a product widthwise direction (a product widthwise direction W) that is perpendicular to the product longitudinal direction; a pair of leg hole openings (leg hole opening 35) being formed; and a pair of leg stretch units (leg stretch units 75) formed around the leg hole openings and can expand and contract in at least the product longitudinal direction, wherein the absorber includes a first region (first region 41) extending from an end at the side of the front waistline region of the absorber towards the side of the crotch region, and a second region (a second region 42) arranged adjacent to the first region at the side of the crotch region from the first region, and having a lower bending rigidity than the first region, and a boundary between the first region and the second region is arranged at the side of the front waistline region from the end at the side of the front waistline region of the leg stretch units, and is arranged at the side of the crotch region from the end at the side of the crotch region of the target unit.

DESCRIPTION OF EMBODIMENTS

Figure 1:
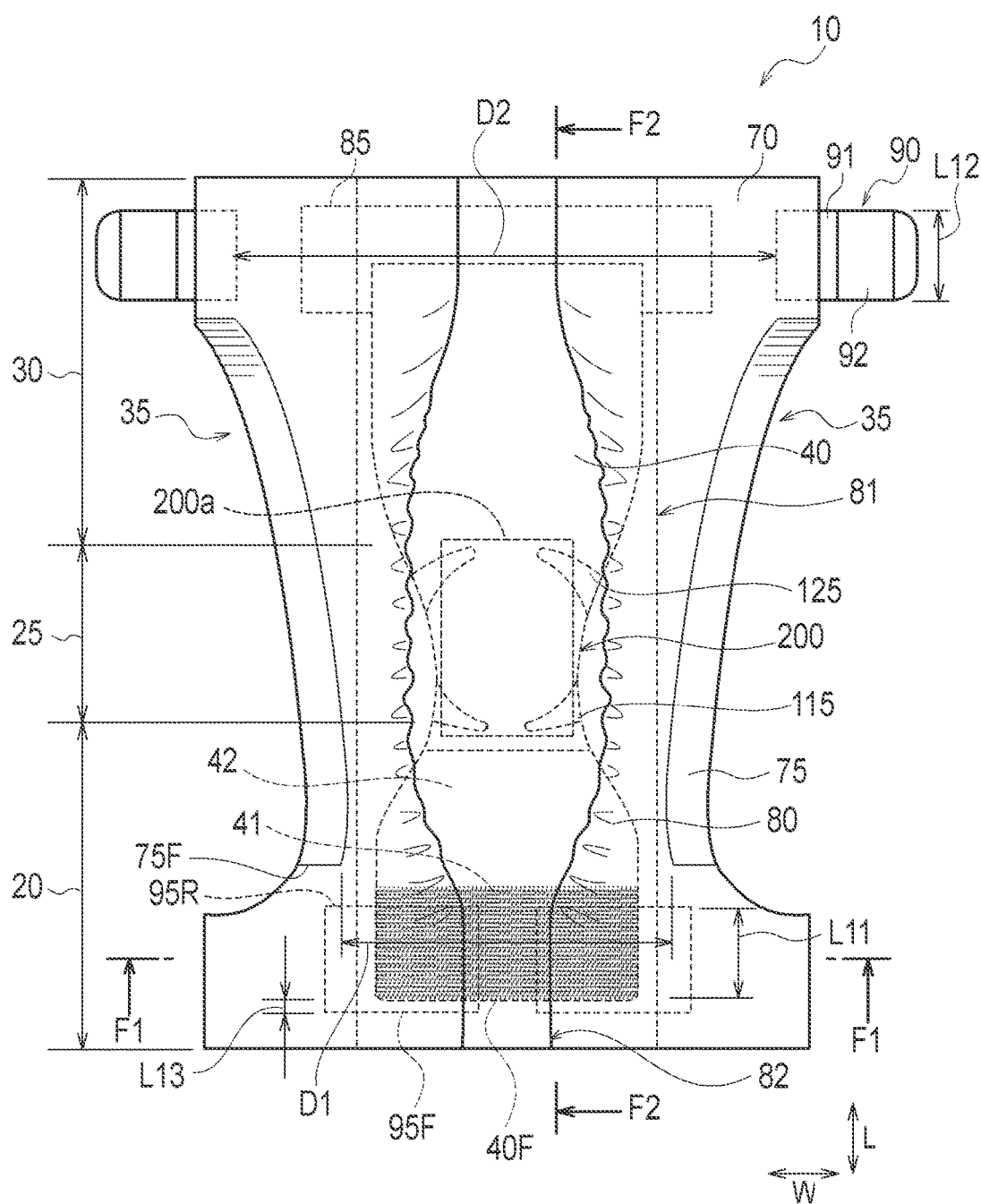
FIG. 1 is an exploded plan view of a disposable diaper according to a present embodiment.

Hereinafter, an embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension are different from the real ones.

Therefore, a specific dimension should be determined in view of the following description. Moreover, among the drawings, the respective dimensional relations or ratios may differ.

(1) Overall Schematic Configuration of Disposable Diaper

Figure 2:
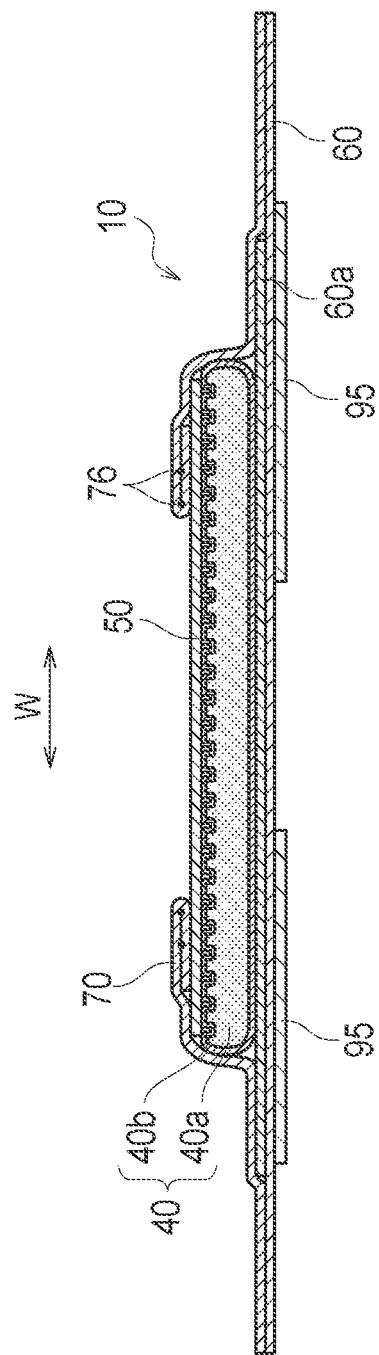
FIG. 2 is a cross-sectional view of the disposable diaper along an F1-F1 line shown in FIG. 1.
Figure 3:
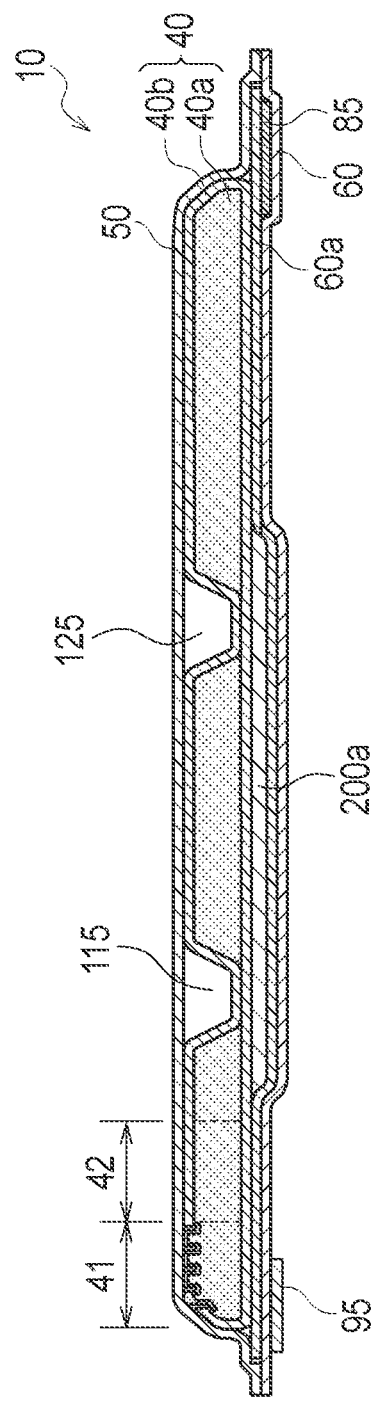
FIG. 3 is a cross-sectional view of the disposable diaper along an F2-F2 line shown in FIG. 1.

FIG. 1 is an exploded plan view of a disposable diaper 10 according to the present embodiment. FIG. 2 is a cross-sectional view of the disposable diaper 10 along an F1-F1 line shown in FIG. 1. FIG. 3 is a cross-sectional view of the disposable diaper 10 along an F2-F2 line shown in FIG. 1. It should be noted that the exploded plan view of FIG. 1 is a diagram in which leg stretch units 75 and leg side gathers 80 are in an expanded state such that wrinkles are not formed in a topsheet 50 and side flaps 70, for example, that configure the disposable diaper 10, but for the sake of description, the leg side gathers 80 are illustrated in a contracted state.

The disposable diaper 10 includes a front waistline region 20, a crotch region 25, and a rear waistline region 30. The front waistline region 20 is a portion that is in contact with the front waistline portion (abdominal portion) of the wearer. Furthermore, the rear waistline region 30 is a portion that is in contact with the rear waistline portion (back portion) of the wearer. The crotch region 25 is positioned between the front waistline region 20 and the rear waistline region 30. Furthermore, a pair of leg hole openings 35 are formed in the disposable diaper 10. The leg hole openings 35, which are provided in the side ends in the widthwise direction of the disposable diaper, correspond to the portion arranged along the area around the legs of the wearer when the disposable diaper is worn by the wearer.

In the present embodiment, the direction from the front waistline portion 20 to the rear waistline portion 30 is called the product longitudinal direction L, and the direction perpendicular to the product longitudinal direction L is called the product widthwise direction W.

The disposable diaper 10 includes an absorber 40 running across the crotch region 25 and extending towards the front waistline region 20 and the rear waistline region 30. The absorber 40 includes an absorbent core 40a and a core wrap 40b.

The absorbent core 40a is the same as that in the conventional disposable diaper, and can be configured appropriately by using well-known components and materials, such as ground pulp and high absorbent polymer. The absorbent core 40a is wrapped by the sheet-like core wrap 40b. The core wrap 40b is a sheet for covering the absorbent core 40a. A part of at least the skin surface side of the core wrap 40b is configured by various nonwoven fabrics or a tissue sheet having permeability. For example, an air-through nonwoven fabric, a spunbond nonwoven fabric, or an SMS (spunbond-meltblown-spunbond) nonwoven fabric having a mass of approximately 10 to 30 g/m2, or a tissue sheet having a mass of approximately 10 to 30 g/m2 can be used.

On the top side (skin contact surface side) of the absorber 40 is provided a liquid-permeable topsheet 50. Furthermore, on the back side (non-skin contact surface side) of the absorber 40 is provided a liquid-impermeable backsheet 60a.

A side flap 70 is provided in each side edge in the product widthwise direction W of the absorber 40. The side flaps 70 are made of one or two or more layers of nonwoven fabrics overlapping one another. Furthermore, a fastening tape 90 is provided in each of the pair of side flaps 70.

The fastening tape 90 extends along the product widthwise direction W in the rear waistline region 30, and holds the disposable diaper 10 onto the body of the wearer by being secured to a target unit 95 of the front waistline region.

The target unit 95 is so configured that at least a part thereof is arranged in the absorber-arranged region in which the absorber is arranged, in the front waistline region, and each of the pair of the fastening tapes 90 is secured onto the target unit. In the present embodiment, a waistline retaining unit is configured by the front waistline region 20, the rear waistline region 30, the target unit 95, and the fastening tape 90.

Furthermore, the disposable diaper 10 includes a crotch stretch unit 200a formed in the crotch region 25 and can expand and contract in the product longitudinal direction L. Specifically, the crotch stretch unit 200a is arranged in a crotch unit 200 formed in the crotch region 25. The configuration of the crotch unit 200 and the crotch stretch unit 200a is described later in detail.

The top side (topsheet 50 side) of the absorber 40 is formed around the leg hole openings 35, and includes a pair of leg stretch units 75 that can expand and contract in the product longitudinal direction L.

The leg stretch units 75 are configured to be longer than the crotch stretch unit 200a in the product longitudinal direction L, and are provided at the outer side from the crotch stretch unit 200a in the product widthwise direction W.

It must be noted that it is sufficient when the leg stretch units 75 are configured such the leg hole openings 35 is stretchable in the product longitudinal direction, and the leg stretch units may be arranged along the leg hole openings 35, or some of the leg stretch units may be arranged in an inclined state with respect to the leg hole openings 35.

Furthermore, the leg stretch units 75 correspond to the portion that is substantially contracted in the product longitudinal direction by a stretchable sheet or the like, and can be conceived as the portion exclusive of the portion in which the stretchable sheet is arranged in a state in which the contractile force is not exhibited.

The leg stretch units 75 of the present embodiment are configured by a stretchable sheet. For example, a stretch film formed by melting a thermoplastic elastomer resin, such as urethane and styrene, and then converting into the shape of a film, a stretchable nonwoven fabric formed from stretchable fibers, or a composite sheet formed by pasting together inextensible sheets that have been partially cut into a stretch film and stretchable nonwoven fabric, or have been made fragile can be used as the stretchable sheet.

Furthermore, instead of the stretchable sheet, a single or a plurality of thread-like or band-like elastic members made of polyurethane elastic fibers and natural rubber may be arranged to configure the leg stretch units 75.

It is preferred that the stretchable sheet configuring the leg stretch units 75 has, at least in the crotch region 25, a width of 5 mm (width in the product widthwise direction W in the natural state of the disposable diaper 10) or more and 45 mm or less, and more preferably 12.5 mm or more and 35 mm or less. When the width is less than 5 mm, the effect of lowering of the load on the skin by the elastic elements achieved by substantially running, in the form of a surface of the leg stretch units, along the area around the legs of the wearer so as to prevent the partial concentration of the securing force is not exhibited, and when the width exceeds 45 mm, the region along the area around the legs becomes too wide in comparison to the length in the product widthwise direction of the entire disposable diaper, and as a result, the stretchable sheet might become entangled at the side of the wearer's body, or may turn over.

The ratio of expansion and contraction of the leg stretch units 75 is preferably 1.6 times to 2.4 times. In the present embodiment, the ratio of expansion and contraction of the leg stretch units 75 is set to 2.0 times.

It is to be noted that a ratio of expansion and contraction means degree of expansion and contraction of the leg stretching unit 75 in an expansion and contraction direction (the product longitudinal direction L in the present embodiment) and is determined as follows.

The ratio of expansion and contraction of the leg gathers 75=(Length of the leg gathers 75 during maximum extension)/(Length of the leg gathers 75 in the natural state)

If the disposable diaper 10 is inserted in a package, take the diaper out of the package, and use a sample that has been kept in such a condition for 12 hours in an ambient temperature of 20° C.±2° C., and a relative humidity of 60%±5% RH.

Next, use a spring measure (tape: covered with glass fiber reinforced vinyl chloride) manufactured by Shinwa Rules Co., Ltd., keep it along the area to be measured, and measure the length of the disposable diaper 10 in this state, that is, the length of the leg gathers 75 when the disposable diaper 10 is in the natural state, and the length of the leg gathers 75 when the disposable diaper 10 is extended from its natural state until wrinkles caused by the elastic members are not visible to the naked eye. The above measurement was performed for 10 samples, and the average value was assumed as the aforementioned length.

Hereinafter, the measurement of the "length" described in the specification will be performed based on the aforementioned measuring method.

Furthermore, the interval between the inner ends of the pair of the left-right leg stretch units 75 in the product widthwise direction W widens from the crotch region 25 towards the front waistline region 20, and also widens from the crotch region 25 towards the rear waistline region 30. By arranging the leg stretch units in a shape that is narrow in the crotch portion and widens towards the front and rear waistlines, the leg stretch units can run along the line of the body because of which the leg stretch units are expanded and arranged appropriately in the area around the legs of the wearer.

Additionally, the interval (D1 in the figure) between the ends of the front waistline region 20 of the pair of left-right leg stretch units 75 is narrower than the interval (D2 in the figure) between the ends of the rear waistline region 30 of the pair of left-right leg stretch units 75. The interval is the distance between the inner ends of the pair of left-right leg stretch units 75 in the product widthwise direction W that is measured after expanding and holding the disposable diaper 10 from the natural state to the state when no wrinkles are formed, in the product longitudinal direction L and the product widthwise direction W.

The extension of the skin surface of the body of the wearer is particularly large in the hip, and is remarkable at a position towards the outer widthwise direction. Furthermore, the leg stretch units 75 are in contact with the body of the wearer. Because D2>D1, even when the movement of the wearer is added to the disposable diaper 10, the leg stretch units 75 in the hip can extend while being in contact with the body, and even when the amount of change in the extension is large, the leg stretch units 75 do not become stiff. Therefore, the shifting of the disposable diaper 10 can be controlled by the leg stretch units 75.

Additionally, in the inner side of the pair of leg stretch units 75 (closer to the center in the product widthwise direction W), a pair of leg side gathers 80 extending along the product lengthwise direction L are provided. The leg side gathers 80, which are provided in the inner ends in the product widthwise direction of the side flaps, are upright stretchable gathers arranged on the inner side in the product widthwise direction from the leg stretch unit. The side flaps are folded back to the side of the topsheet in the inner ends in the product widthwise direction and are formed by laminating two layers. Elastic members 76 (see FIG. 2) are provided between the two-layered side flaps in an expanded state in the longitudinal direction. The leg side gathers 80 are formed by the side flaps 70 and the elastic members 76.

The leg side gathers 80 have a joining portion 81 that is joined with the backsheet 60*a*, and a free end portion 82 positioned on the opposite side of the joining portion 81 and in which the elastic members (not shown in FIG. 1) are arranged. As for the leg side gathers 80, when the diaper is worn, the joining portion 81 rises up as the proximal end and the free end portion 82 is in contact with the skin of the wearer as the apex.

The backsheet 60*a*, which is arranged between the absorber 40 and an exterior sheet 60 functions as a leakage-preventing sheet.

Furthermore, the end of the free end portion 82 of the leg side gathers 80 in the product longitudinal direction L is joined with the topsheet 50. The joining portion 81 is arranged between the crotch stretch unit 200*a* and the leg stretch unit 75, in the product widthwise direction W.

Various types of configurations can be adopted for the joining portion 81 of the leg side gathers 80. The joining portion, for example, is configured to be an upright proximal end, and could be a portion extending from the crotch portion to the front waistline region and the rear waistline region in the product longitudinal direction and joined with the topsheet, or a portion joined with the liquid-impermeable backsheet and the exterior sheet in the outer side in the widthwise direction from the absorbent core 40*a*.

Furthermore, the leg side gathers are not limited to the above configuration as long as the leg side gathers are upright gathers arranged on the inner side in the product widthwise direction from the leg stretch unit, and any configuration of the leg side gathers that is well-known in the conventional art can surely be adopted.

Furthermore, the disposable diaper 10 includes a lower-back stretch unit 85 formed in the rear waistline region 30 and can expand and contract in the product widthwise direction W.

The member configuring the lower-back stretch unit 85 is not particularly restricted, but a member that is as thin as possible with a low rigidity, and has a small reduction in width, for example, a stretch film, is preferably used.

After being extended up to 1.5 to 2.5 times the length in the non-expanded state (natural state), the lower-back stretch unit 85 is adhered onto the exterior sheet 60 with a hot-melt adhesive or heat processing.

In the present embodiment, the lower-back stretch unit 85 is arranged between the exterior sheet 60 and the back sheet 60*a* (see FIG. 3). However, if the core wrap 40*b* is configured to extend in the outer side in the product longitudinal direction from the absorbent core 40*a*, the lower-back stretch unit 85 may be arranged between the core wrap 40*b* and the backsheet 60*a* or exterior sheet 60. The position of the lower-back stretch unit is not particularly restricted, but preferably, the lower-back stretch unit is arranged at the non-skin contact surface side from the absorber 40. Furthermore, in a region in which the absorber is not arranged, the lower-back stretch unit may be arranged between the side flaps 70 and the backsheet 60*a* or exterior sheet 60.

In the plan view, the lower-back stretch unit 85 is arranged between the pair of fastening tapes. The lower-back stretch unit 85 contracts the space between the fastening tapes in the widthwise direction.

The lower-back stretch unit according to the present embodiment is configured to stretch in the product widthwise direction, however, the lower-back stretch unit may be configured to stretch in the product widthwise direction and the product longitudinal direction.

(2) Shape of Absorber

Next, the shape of the absorber 40 will be described.

Figure 4A:
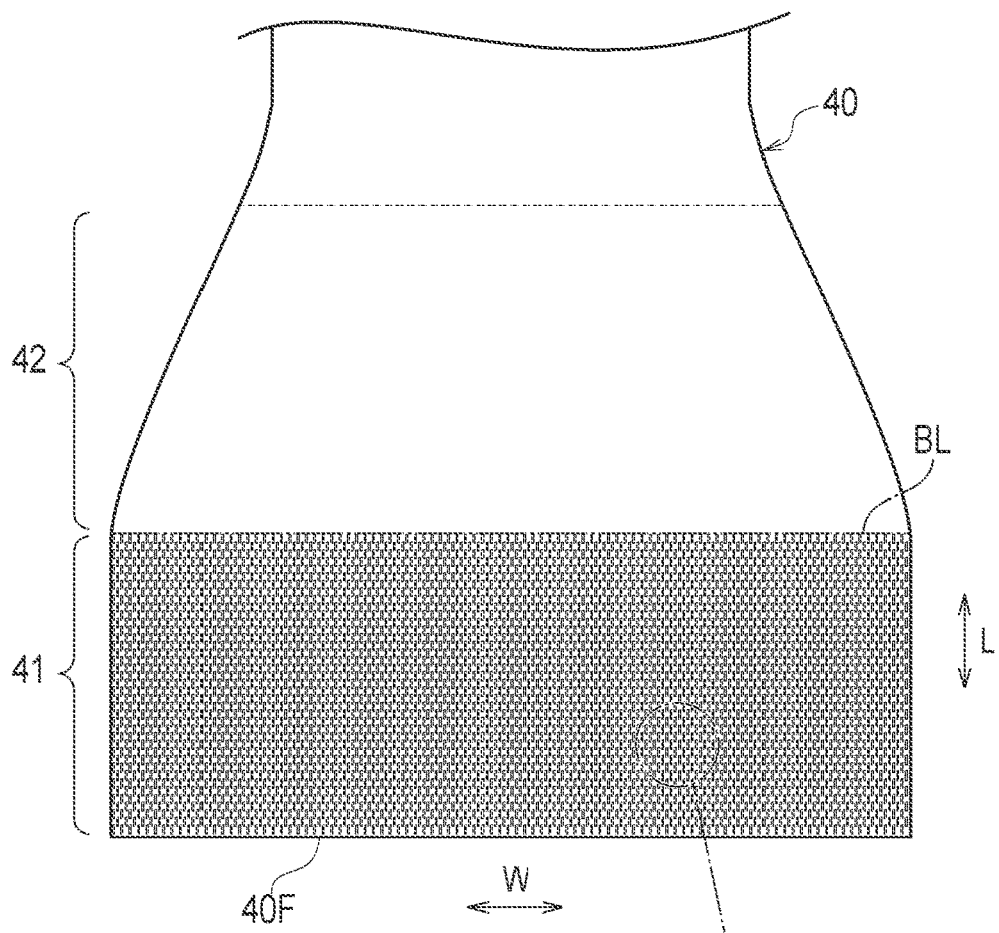
FIG. 4A is an enlarged plan view of an absorber according to the present embodiment.
Figure 4B:
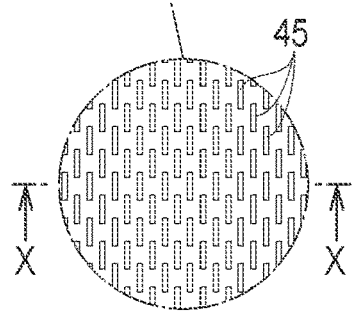
FIG. 4B is a partial enlarged plan view of FIG. 4A.
Figure 4C:
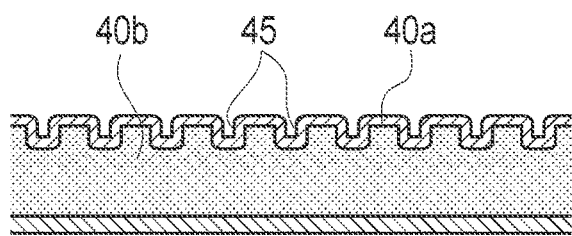
FIG. 4C is a view of the X-X cross-section of FIG. 4B.

FIGS. 4A, 4B, and 4C are diagrams illustrating the absorber 40. FIG. 4A is an enlarged plan view as seen from the topsheet 50 side, FIG. 4B is a partial enlarged view of FIG. 4A, and FIG. 4C is a view of the X-X cross-section of FIG. 4B.

The absorber 40 includes a first region 41 extending from an end 40F at the side of the front waistline region of the absorber in the product longitudinal direction towards the side of the crotch region, and a second region 42 arranged adjacent to the first region 41 at the side of the crotch region from the first region 41.

The first region 41 is provided in the entire absorber in the product widthwise direction. In the first region 41, a compressed unit 45 in which the absorber 40 is compressed in the product thickness direction is formed. A plurality of the compressed units 45 are formed intermittently across the entire first region. On the other hand, the compressed units 45 are not formed in the second region 42. Thus, the bending rigidity of the first region 41 is configured to be higher than the bending rigidity of the second region 42.

The bending rigidity in the present embodiment is based on the rigidity value conforming to the Taber method (JISP8125), and can also be checked by measuring as described below. First of all, with the disposable diaper in the expanded state, a sample of the portion where the bending rigidity is to be measured (for example, the absorber) is extracted. As regards the sample, the portion to be measured is prepared with the dimensions of 70 mm sample length×38 mm in the widthwise direction perpendicular to the sample length direction, along the product widthwise direction or the product longitudinal direction. If a stretchable elastic member is included in the sample, the elastic member is removed. The Taber Stiffness Tester manufactured by Yasuda Seiki Seisakusho Ltd. is used for measuring the rigidity value. 10 samples are taken and measurement is performed for each sample, and the average value is set as the rigidity value.

The measurement procedure is as described in (a) through (e) below.

(a) Measure the thickness (A) of the extracted samples.
(b) Next, insert the sample such that the sample is in contact with the center of the chuck (lower) of the tester.
(c) Adjust the total left-right interval between the support roller and the sample to (A)×0.80 (mm)
(d) Appropriately select an auxiliary weight such that the specified load scale is in the range of 15 to 85% of the maximum scale.
(e) Rotate the samples in both left and right directions, stop at the point where the 15° support marked line and the central marking of the pendulum match, and read the value on the tester. Consider the value on the left side of the scale as (B) and the value on the right side of the scale as (C).

The rigidity value is calculated by the below formula:

$$\text{Rigidity value}(mN \cdot m) = (((B)+(C))/2) \times (\text{Auxiliary weight coefficient}) \times 9.81 \times 10^{-2} \quad \text{Formula:}$$

If a width of 38 mm cannot be acquired for the specimen, perform conversion to the bending moment of 38-mm width.

The higher the rigidity value thus measured, the higher the bending rigidity, and the lower the rigidity value, the lower the bending rigidity.

The plurality of compressed units 45 are arranged in a staggered manner, and are configured such that the length in the product longitudinal direction is more than the length in the product widthwise direction. Thus, because the compressed units 45 are arranged discontinuously in a staggered manner, compressed portions and uncompressed portions co-exist in the first region 41. The uncompressed portions have a lower bending rigidity than the compressed portions and can be deformed flexibly, because of which the bending rigidity of the first region 41 can be increased, and the first region 41 can be arranged along the line of the body having a roundness.

It must be noted that when the absorbent core 40a has been wrapped by the core wrap 40b, the compressed units 45 may be compressed and formed in the thickness direction from the outer side of the core wrap 40b, or when the absorbent material configuring the absorbent core 40a is laminated, the basis weight of the absorbent material of the first region 41 may be set higher than that of the absorbent material of the second region 42, and the compressed units may be formed by compressing the absorbent core 40a in the thickness direction.

The absorber according to the present embodiment has been configured such that the bending rigidity in the first region 41 is higher due to the formation of the compressing units 45, however, the bending rigidity in the first region 41 may be configured to be higher than that in the second region 42 based on some other configuration as well.

The boundary between the first region 41 and the second region 42 is arranged along the product widthwise direction W. A boundary line BL that virtually illustrates the boundary between the first region 41 and the second region 42 is shown in FIG. 4A. Furthermore, as illustrated in FIG. 1, the boundary between the first region 41 and the second region 42 is arranged at the side of the front waistline region from an end 75F at the side of the front waistline region of the leg stretch units 75, and is arranged at the side of the crotch region from an end 95R at the side of the rear waistline region of the target unit 95.

The boundary between the first region 41 and the second region 42 is the portion where the bending rigidity of the absorber 40 is different, and forms an inflection portion where the absorber bends easily. Thus, when an external force for deforming the absorber is applied, the absorber easily deforms with the boundary between the first region 41 and the second region 42 as the base point.

Figure 5A:
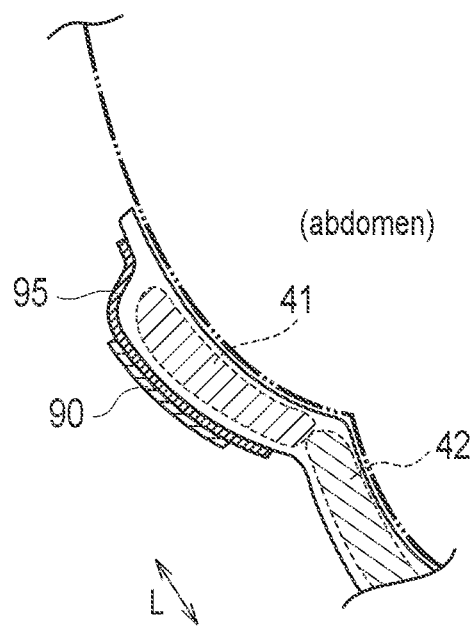
FIG. 5A is a diagram schematically illustrating the state when the disposable diaper according to the present embodiment is worn by a wearer.
Figure 5B:
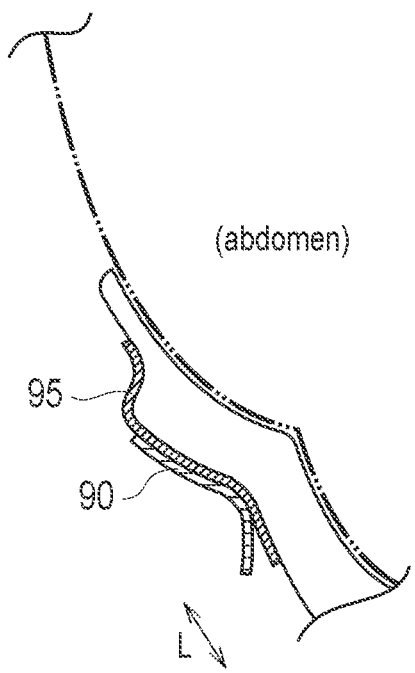
FIG. 5B is a state when a conventional disposable diaper according to a comparative example is worn by a wearer.

Next, the folds formed around the abdomen of the wearer in the case of the disposable diaper according to the present embodiment and the disposable diaper according to a comparative example will be explained. FIGS. 5A and 5B are diagrams schematically illustrating the state when the disposable diaper according to the present embodiment is worn by a wearer. FIGS. 5A and 5B schematically illustrate the cross-section of the sides when the disposable diaper is worn. FIG. 5A is the state when the disposable diaper according to the present embodiment is worn, and FIG. 5B is a state when a conventional disposable diaper according to a comparative example is worn. In the conventional disposable diaper, the bending rigidity of the absorber is uniform, and the first region and second region are not provided.

In the disposable diaper, the secured portion where the fastening tape 90 is secured to the target unit 95 is fit to the lower back of the wearer, and the state of wearing the diaper is maintained. Because the secured portion between the fastening tape 90 and the target unit 95 is positioned in the ventral side of the wearer, as shown in FIG. 5 B, the securing portion is compressed with his abdomen when the wearer is sitting or bends forward resulting in the formation of folds.

Particularly, as compared to an adult, an infant and toddler mostly has a body type with a bulging abdomen, and when an open-type disposable diaper is worn by such an infant and toddler, the secured portion between the fastening tape and the target unit is compressed due to the bulging of the abdomen, making it easy for folds to form.

For example, when folds are formed in the target unit, the fastening tape sometimes rises partially from the target unit due to the folds. In this way, there is a possibility that if the fastening tape rises partially from the target unit, then the fastening tape may be unsecured.

In contrast, in the disposable diaper according to the present embodiment, a first region having a relatively higher bending rigidity, and a second region having a lower bending rigidity than the first region are provided in the absorber, and the boundary between the first region and the second region is arranged at the side of the rear waistline region from the target unit. Thus, the boundary, where the bending rigidity of the absorber is different, is positioned on the inner side in the longitudinal direction from the target unit.

Therefore, for example, even if the securing portion of the fastening tape is compressed by the abdomen of the toddler or infant, folds are formed intentionally in the boundary where the bending rigidity of the absorber is different, and the formation of folds in the secured portion between the fastening tape and the target unit can be made difficult. As in the conventional art, because the secured state can be maintained without increasing the engagement strength, the secured state of the fastening tape can be maintained while preventing stimulation to the skin.

(3) Configuration of Fastening Tape and Target Unit

As shown in FIG. 1, the fastening tape 90 is installed in the region of the side flaps 70 corresponding to the rear waistline region 30. The fastening tape 90 includes a base sheet 91 connected with the side flaps 70, and a hook sheet 92 provided with a plurality of engagement hooks (not shown in the figure), and fixed onto the base sheet 91.

The hook sheet 92 is fixed, specifically, joined with the base sheet 91. The hook sheet 92 and the base sheet 91 are preferably joined such that the rigidity of the fastening tape 90 does not become more than necessary. Specifically, the hook sheet 92 and the base sheet 91 are preferably joined by a hot-melt adhesive applied intermittently in dot shape, line shape, or spiral shape. The hook sheet 92 and the base sheet 91 may also be joined with a heat seal, for example.

The base sheet 91 is configured by one layer of nonwoven fabrics or two or more plurality of layers of nonwoven fabrics overlapping one another. A nonwoven fabric manufactured by a manufacturing method such as spun bond (SB) or spun bond-melt blown-spun bond (SMS) can be used as the base sheet 91. The basis weight of the nonwoven fabric (or total basis weight in the case of a plurality of layers) configuring the base sheet 91 is 20 to 120 g/m2, and preferably 40 to 90 g/m2. When there are a plurality of layers of the nonwoven fabric configuring the base sheet 91, the basis weight per layer is 0 to 80 g/m2, preferably 15 to 60 g/m2, and more preferably 20 to 55 g/m2.

The target unit 95 is provided at the non-skin contact surface side of the exterior sheet 60 of the front waistline region. The target unit 95, which is configured such that the engagement hooks of the fastening tape are engaged therein, functions as the loop in a hook-and-loop locking system. An air-through nonwoven fabric, for example, can be used as the target unit.

A fibrous nonwoven fabric prepared from polyolefin-based thermoplastic synthetic resin fibers, or a polyolefin-based thermoplastic synthetic resin film, for example, can be used for the target unit 95. Furthermore, the loop provided in the target unit can be formed by a polyolefin-based thermoplastic synthetic resin.

In addition, a bulky nonwoven fabric, which is embossed partially to prevent fluffing on the surface of the nonwoven fabric may be used as the target unit 95.

Furthermore, the target unit can also be formed by forming the exterior sheet 60 of the disposable diaper with a nonwoven fabric, and then printing a design showing the position of attaching the fastening tape 90 on the non-skin contact surface side of the exterior sheet 60, or by arranging the sheet with a design on the non-skin contact surface side of the exterior sheet 60.

The target unit is arranged by partially overlapping the absorber in the product thickness direction. Thus, a length L11 in the product longitudinal direction of the laminated region, where the target unit and the absorber overlap, is configured to be more than a length L12 in the product longitudinal direction of the hook sheet.

Because the laminated region, where the fastening tape and the absorber overlap, in the product longitudinal direction, is longer than the hook sheet of the fastening tape, it is possible to arrange the entire hook sheet on the region where the fastening tape and the absorber overlap. Thus, the engagement state of the hook sheet is easy to be maintained while easily maintaining the hook sheet in a flat state.

In a configuration in which the length of the hook sheet in the product longitudinal direction changes in the product widthwise direction, it is sufficient if the length of the laminated region in the product longitudinal direction is configured to be longer than the shortest length of the hook sheet in the product longitudinal direction.

In addition, it is preferable that the length of the laminated region, where the target unit and the absorber overlap, in the product longitudinal direction is desired to be 60% or more of the length of the target unit in the longitudinal direction. This is because if the length is less than 60%, the securing force that holds the absorber 40 with the fastening tape 90 is insufficient, which may give rise to the problem of the fastening tape 90 unsecuring from the target unit 95.

Furthermore, the length L12 of the hook sheet in the product longitudinal direction is configured to be longer than a distance L13 between the end 40F at the side of the front waistline region of the absorber and an end 95F at the side of the front waistline region of the target unit.

Because the length L12 of the hook sheet is longer than the distance between end at the side of the front waistline region of the absorber and the end at the side of the front waistline region of the target unit, the hook sheet is always positioned on the absorber when placing the hook sheet on the fastening tape. By placing the fastening tape on the absorber having a relatively high rigidity, it becomes easy to maintain the engagement state of the hook sheet.

Furthermore, the lower-back stretch unit 85 can expand and contract in the product widthwise direction is provided between the pair of fastening tapes in the product widthwise direction.

By providing the lower-back stretch unit 85 between the fastening tapes 90, the lower back where the fastening tape is secured is brought in close contact, a crease is provided at the desired location (boundary between the first region and the second region), and the formation of a crease in the locking portion of the fastening tape, etc. can be prevented.

(4) Shape of Crotch Unit

Next, the shape of the crotch unit 200 will be described. As described above, the crotch unit 200 includes the crotch stretch unit 200a. The crotch stretch unit 200a is configured to be easily maintained in a flat shape as compared to the other portions of the absorber 40 at the time of wearing the disposable diaper. The crotch unit 200 includes the crotch stretch unit 200a that can be stretched in at least the product longitudinal direction L or the product widthwise direction W.

The crotch stretch unit 200a is provided separately and independently of the leg stretch unit 75, and is configured to contract 60% or more of the length in the widthwise direction of the absorbent core 40a in the position where the crotch stretch unit overlaps the absorbent core 40a (in the present embodiment, it is the position between the core wrap 40b that wraps the absorbent core 40a and the backsheet 60a). In this way, due to the contraction of the portion in which the absorbent core 40a is arranged by the crotch stretch unit 200a, the absorbent core 40a is constricted, and a flat shape is easily maintained as compared to the portion where the absorbent core 40a is not constricted.

On the other hand, the absorbent core 40a positioned in the front waistline region and the rear waistline region positioned on the outer side in the product longitudinal direction from the crotch stretch unit 200a is not contracted by the crotch stretch unit 200a, because of which the crotch unit 200 is arranged appropriately along the body without the entire absorber coming in excessively close contact with the body.

Furthermore, because the crotch unit 200 can be stretched along the product longitudinal direction L, the front waistline region 20 and the rear waistline region 30 rise up easily due to the contraction of the crotch unit 200, and at the time of wearing the diaper, a flat crotch region is formed along the body at the crotch of the wearer. Because the front waistline region and the rear waistline region rise up from the crotch stretch unit 200a, the fitting of the disposable diaper 10 on the wearer improves. The crotch stretch unit 200a is preferably configured by a stretchable sheet. By configuring the crotch stretch unit 200a by a stretchable sheet, the absorbent core 40a of the region in which the stretchable sheet is arranged is constricted uniformly, and maintaining a flat shape becomes easier. It must be noted that the stretchable sheet, for example, can be configured by the same stretchable sheet as the leg stretch unit 75.

Furthermore, rather than the stretchable sheet, the crotch stretch unit 200a can also be configured by arranging a plurality of thread-like or band-like elastic members made from polyurethane elastic fibers and natural rubber. In this case, in order to uniformly constrict the absorbent core 40a by the crotch stretch unit 200a, the interval between the elastic members is preferably 7 mm or less, and more preferably 5 mm or less. Furthermore, in order to uniformly constrict the absorbent core 40a, the difference in the interval between adjacent elastic members is desired to be 0.5 mm or less.

Furthermore, the ratio of expansion and contraction of the crotch stretch unit 200a is preferably 1.2 times or more and 1.8 times or less, specifically. In the present embodiment, the ratio of expansion and contraction of the crotch stretch unit 200a is set to 1.4 times.

The ratio of expansion and contraction of the crotch stretch unit 200a implies the extent of the expansion and contraction of the crotch stretch unit 200a in the direction of expansion and contraction (product longitudinal direction L), and is stipulated as below:

> The ratio of expansion and contraction of crotch stretch unit 200a=(Length of the crotch unit during maximum extension)/(Length of the crotch unit in the natural state)

Firstly, in a case where the disposable diaper 10 is inserted in a package, for example, then the disposable diaper 10 is taken out of the package, and the diaper is kept in such a condition for 60 minutes in an ambient atmosphere having a temperature of 20° C.±2° C., and a relative humidity of 60%±5% RH, and then a length of the crotch stretch unit is measured i in the direction of expansion and contraction. This length is set to a "length i in the direction of expansion and contraction of the crotch stretch unit 200a in the natural state".

Secondly, measurement is performed with respect to the length in the direction of expansion and contraction of the desired region in this state (that is, in the natural state), and the length in the direction of expansion and contraction of the desired region when the disposable diaper is extended from its natural state to a state in which wrinkles caused by the elastic members cannot be visually confirmed. This length is set to a "length in the direction of expansion and contraction of the crotch stretch unit 200a in the maximum extended state"

By thus setting the ratio of expansion and contraction of the crotch stretch unit 200a between 1.2 times and 1.8 times, it is possible to favorably follow the stretching of the skin of the wearer.

For example, when the wearer bends forward such that the front side of the body constricts, there exists a part in the skin at the side of the hip portion of the wearer that stretches by approximately 30% as compared to the state when the body has been stretched out.

That is, when the ratio of expansion and contraction of the crotch stretch unit 200a is 1.2 times or less, the contraction of the crotch stretch unit 200a in the natural state of the disposable diaper is insufficient, and as compared to the case when the crotch stretch unit 200a has not been provided, the difference in the ease of curving of the disposable diaper 10 is small because of which the front waistline region 20 does not rise at the desired position.

On the other hand, when the ratio of expansion and contraction of the crotch stretch unit 200a is more than 1.8 times, the contraction size in the contracting direction of the crotch stretch unit 200a becomes too large, because of which the region where the crotch stretch unit 200a exists easily comes in close contact with the body of the wearer rather than running along it, and the disposable diaper 10 easily shifts to the lower side of the wearer.

Furthermore, the center of the crotch stretch unit 200a in the product longitudinal direction L is arranged at the side of the front waistline region 20 from the center of the disposable diaper 10 in the product longitudinal direction L. However, the crotch stretch unit 200a is arranged to run across the center of the disposable diaper 10 in the product longitudinal direction L.

In such a case, in view of the rigidity of the absorber core 40*a* and the rigidity of other members configuring the disposable diaper 10, the thickness of the elastic members and the arrangement pitch can be selected appropriately, however, when the main body of the disposable diaper 10 is in the natural state (unextended state), the entire side edge in the product widthwise direction W of the absorber core 40*a* is preferable to be in a contracted state.

Furthermore, a notch 115 (notch 125) is formed in the crotch region of the absorber 40. The notch 115 and the notch 125 correspond to a region in which the absorbent core 40*a* configuring the absorber 40 does not exist. In the present embodiment, the notch 115 and the notch 125 correspond to a low rigidity unit in which the basis weight of the absorbent core 40*a* is lower than that of the other portion of the absorbent core 40*a*. It should be noted that instead of forming the notch 115 and the notch 125, the region of the notch 115 and the notch 125 may be such that the basis weight of the absorbent core 40*a* is lower than that of the other portion of the absorbent core 40*a*.

The notch 115 and the notch 125 exist along the edges in the product longitudinal direction L of the crotch unit 200. It should be noted that even though the notch 115 and the notch 125 are formed, the absorbent core 40*a* positioned in the front waistline region 20 and the rear waistline region 30, and the absorbent core 40*a* positioned in the crotch region 25 are preferred to be in continuation, particularly in the widthwise direction, rather than being completely separate.

As the notch 115 and the notch 125 run towards the outer side in the product widthwise direction W, the length in the product longitudinal direction L keeps on widening. As a result of such a shape, the outer side in the product widthwise direction W of the absorber core 40*a* is constricted more easily, and a flat "bottom unit" is formed more easily. Furthermore, the absorbent core 40*a* positioned towards the front waistline region 20 from the notch 115, and the absorbent core 40*a* positioned towards the rear waistline region 30 from the notch 125 rise up from the "bottom unit", and can easily curve along the roundness of the body of the wearer (the abdominal portion and the hip), because of which the shape of the disposable diaper can be brought closer to the body of the wearer.

Furthermore, the edge towards the front waistline region 20 (rear waistline region 30) of the notch 115 (notch 125) is arc shaped. The shape of the edge of the notch 115 (notch 125) is such that the center of the arc is positioned in the rear waistline region 30 (front waistline region 20) from the edge. As a result of such a shape, the deformation along the roundness of the body of the wearer occurs more easily and remarkably.

(5) Operation and Effect

In the absorber, a first region having a relatively higher bending rigidity, and a second region having a lower bending rigidity than the first region are provided, and the boundary between the first region and the second region is arranged at the side of the front waistline region from the target unit. Thus, the boundary, where the rigidity of the absorber is different, is positioned on the inner side in the longitudinal direction from the target unit.

Therefore, for example, even if the securing portion of the fastening tape is compressed by the stomach of the toddler or infant, folds are formed intentionally in the boundary where the bending rigidity of the absorber is different, and the formation of folds in the secured portion between the fastening tape and the target unit can be made difficult. As in the conventional art, because the securing state can be maintained without increasing the engagement strength, the secured state of the fastening tape can be maintained while preventing stimulation to the skin.

In addition, the boundary between the first region and the second region, where folds are formed, is positioned towards the front from the leg stretch units. For example, if the leg stretch units and the boundary overlap, folds are formed in the leg stretch unit, and the leg hole openings might not be arranged along the area around the legs. However, because the folds are formed easily at a location away from the leg stretch units, even when the wearer moves, folds are formed while maintaining the state of close contact between the leg stretch units 75 and the area around the legs, and the secured state between the fastening tape and the target unit can be maintained.

Furthermore, a plurality of compressed units of the disposable diaper 10 are formed intermittently across the entire first region. Thus, the rigidity of the entire first region can be increased in an almost uniform manner. Also, because a plurality of compressed units are arranged intermittently in the first region, compressed portions and uncompressed portions co-exist in the first region. The uncompressed portions have a lower rigidity than the compressed portions and can be deformed flexibly, because of which the rigidity of the first region 41 can be increased, and the first region 41 can be arranged along the line of the body having a roundness.

Furthermore, because the laminated region, where the fastening tape and the absorber overlap, is longer than the hook sheet of the fastening tape, it is possible to arrange the entire hook sheet on the region where the fastening tape and the absorber overlap. Thus, the hook sheet is easily maintained in a flat state, and the secured state between the hook sheet and the target unit is easy to be maintained.

Because the length of the hook sheet is longer than the distance between end at the side of the front waistline region of the absorber and the end at the side of the front waistline region of the target unit, the hook sheet is always positioned on the absorber when placing the hook sheet on the fastening tape. By placing the fastening tape on the absorber having a relatively high rigidity, it becomes easy to maintain the engagement state of the hook sheet.

In addition, by providing the lower-back stretch unit between the pair of fastening tapes, the lower back where the fastening tape is secured is brought in close contact, a crease is provided at the desired location (boundary between the first region and the second region), and the formation of a crease in the locking portion of the fastening tape, etc. can be prevented.

Because the crotch stretch unit 200*a* is provided in the absorber of the crotch region, even when the absorber of the crotch region is pressed by the legs of the wearer from the outer side in the widthwise direction towards the inner side in the widthwise direction, the deformation can be absorbed in the crotch stretch unit 200*a*. For example, when the crotch stretch unit 200*a* is not provided, and folds are formed from the crotch region towards the side of the front waistline region, folds are formed in the target unit at the side of the front waistline region, and the secured state between the fastening tape and the target unit may be lost. However, by providing the crotch stretch unit, it becomes difficult for folds to be formed in the front waistline region, and the secured state between the fastening tape and the target unit is easily maintained.

(6) Other Embodiments

As described above, the present invention is disclosed through the above embodiments of the present invention. However, it should not be interpreted that the statements and drawings constituting a part of the present disclosure limit the present invention. From this disclosure, a variety of alternate embodiments, examples, and applicable techniques will become apparent to one skilled in the art.

In the aforementioned embodiment, an open-type disposable diaper was described as an example, however, the present invention is also applicable to a pant-type disposable diaper. As regards a pant-type diaper having a waistline opening unit and a pair of leg hole opening units formed by joining both left-right edges of an outer-layer sheet forming the front waistline region and the rear waistline region, the outer-layer sheet of the front waistline region and the rear waistline region includes elastic elements that can be expanded and constructed in the product widthwise direction W, and by constructing the elastic elements, the disposable diaper is held in the waistline of the wearer. That is, the area in which both left-right edges extending in the product longitudinal direction L are joined becomes the waistline retaining unit.

Furthermore, in the disposable diaper according to the modification, rather than leg gathers formed from an elastic nonwoven sheet, leg gathers formed from thread-like elastic members may be provided.

As described above, it is of course that the present invention includes various embodiments and the like not described here. Therefore, the technical range of the present invention is to be defined only by the inventive specific matter according to the adequate claims from the above description.

The entire contents of Japanese Patent Application No. 2012-081143 (filed on Mar. 30, 2012) are incorporated in the present specification by reference.

INDUSTRIAL APPLICABILITY

It is possible to provide a disposable diaper, with which it is possible to maintain the secured state of the fastening tape while preventing stimulation to the skin of the wearer.

REFERENCE SIGNS LIST

10 . . . disposable diaper
20 . . . Front waistline region
25 . . . Crotch region
30 . . . Rear waistline region
35 . . . Leg hole openings
40 . . . Absorber
40a . . . Absorbent core
40b . . . Core wrap
41 . . . First region
42 . . . Second region
45 . . . Compressed unit
50 . . . Topsheet
60 . . . Exterior sheet
60a . . . Backsheet
70 . . . Side flaps
75 . . . Leg stretch unit
80 . . . Leg side gathers
81 . . . Joining portion
82 . . . Free end portion
90 . . . Fastening tape
91 . . . Base sheet
92 . . . Hook sheet
95 . . . Target unit
115 . . . Notch
125 . . . Notch
200 . . . Crotch unit
200a . . . Crotch stretch unit
BL . . . Boundary line
L . . . Product longitudinal direction
W . . . Product widthwise direction

The invention claimed is:

1. A disposable diaper, comprising:
a front waistline region;
a rear waistline region;
a crotch region positioned between the front waistline region and the rear waistline region;
a product longitudinal direction from the front waistline region towards the rear waistline region;
a product widthwise direction perpendicular to the product longitudinal direction;
an absorber running across the crotch region and extending in the front waistline region and the rear waistline region;
a pair of fastening tapes extending from the rear waistline region outwardly in the product widthwise direction;
a target unit arranged at least partially in an absorber-arranged region in which the absorber is arranged, wherein the target unit is arranged in the front waistline region and each of the fastening tapes is configured to be secured on the target unit;
a pair of leg hole openings; and
a pair of leg stretch units extending around the leg hole openings and configured to expand and contract in at least the product longitudinal direction,
wherein, in the product longitudinal direction, the absorber includes
a first region extending from a front end of the absorber in the front waistline region towards the crotch region,
a second region adjacent to a rear end of the first region, and having a lower bending rigidity than the first region, and
a boundary between the first region and the second region, said boundary arranged between front ends of the leg stretch units and a rear end of the target unit.

2. The disposable diaper according to claim 1, wherein each of the fastening tapes has
a base sheet connected to the rear waistline region, and
a hook sheet provided with a plurality of engagement hooks and fixed onto the base sheet,
the absorber and the target unit overlap in a product thickness direction in a laminated region, the product thickness direction perpendicular to both the product widthwise direction and the product longitudinal direction, and
a length of the laminated region in the product longitudinal direction is more than a length of the hook sheet in the product longitudinal direction.

3. The disposable diaper according to claim 1, wherein each of the fastening tapes has
a base sheet connected to the rear waistline region, and
a hook sheet provided with a plurality of engagement hooks and fixed onto the base sheet, and
a length of the hook sheet in the product longitudinal direction is more than a distance between the front end of the absorber and a front end of the target unit in the product longitudinal direction.

4. The disposable diaper according to claim 1, wherein the absorber includes front and rear peripheral edges opposing each other in the product longitudinal direction, the front peripheral edge is in the front end of the absorber, and the first region of the absorber extends from the front peripheral edge of the absorber toward the rear peripheral edge of the absorber in the product longitudinal direction.

5. The disposable diaper according to claim 1, wherein an entirety of the first region is located forward of the leg stretch units in the product longitudinal direction.

6. The disposable diaper according to claim 1, wherein a distance between rear ends of the leg stretch units in the product widthwise direction is greater than a distance between the front ends of the leg stretch units in the product widthwise direction.

* * * * *